(12) United States Patent
Chang et al.

(10) Patent No.: US 7,385,041 B2
(45) Date of Patent: Jun. 10, 2008

(54) DUAL FUNCTIONING EXCIPIENT FOR METAL CHELATE CONTRAST AGENTS

(75) Inventors: C. Allen Chang, Cupertino, CA (US); Krishan Kumar, East Windsor, NJ (US); Michael F. Tweedle, Princeton, NJ (US)

(73) Assignee: Bracco International B.V., Amsterdam (NL)

( * ) Notice: Subject to any disclaimer, the term of this patent is extended or adjusted under 35 U.S.C. 154(b) by 167 days.

(21) Appl. No.: 10/787,526

(22) Filed: Feb. 26, 2004

(65) Prior Publication Data

US 2004/0170566 A1 Sep. 2, 2004

Related U.S. Application Data

(63) Continuation of application No. 08/032,763, filed on Mar. 15, 1993, now abandoned, which is a continuation of application No. 07/682,487, filed on Apr. 9, 1991, now abandoned, which is a continuation-in-part of application No. 07/514,468, filed on Apr. 25, 1990, now abandoned.

(51) Int. Cl.
*C07F 13/00* (2006.01)

(52) U.S. Cl. .......... 534/14; 534/10; 424/1.11; 424/1.65; 424/1.69; 424/9.1; 424/9.3; 424/9.4; 424/9.5

(58) Field of Classification Search ........ 424/1.11, 424/1.65, 9.1, 9.3, 9.32, 9.4, 9.321, 9.323, 424/9.36, 9.364, 9.365, 9.42, 9.5, 9.6; 534/7, 534/10–16
See application file for complete search history.

(56) References Cited

U.S. PATENT DOCUMENTS 4,016,290 A * 4/1977 Rahman .............. 514/566

FOREIGN PATENT DOCUMENTS

WO    WO 89/00052    * 1/1989

* cited by examiner

*Primary Examiner*—Dameron L. Jones
(74) *Attorney, Agent, or Firm*—Kramer Levin Naftalis & Frankel LLP

(57) ABSTRACT

A novel dual functioning excipient for metal chelate contrast agents is disclosed. The present excipient, $$X_m[X'(L')]_n,$$

which is the calcium or zinc salt of the calcium or zinc complex of an organic ligand, enhances safety in that it is able to scavenge both free metal ions and free organic ligand.

6 Claims, No Drawings

DUAL FUNCTIONING EXCIPIENT FOR METAL CHELATE CONTRAST AGENTS

This is a continuation of U.S. application Ser. No. 08/032,763, filed Mar. 15, 1993, now abandoned which is a continuation of U.S. application Ser. No. 07/682,487, filed Apr. 9, 1991, now abandoned which is a continuation-in-part of U.S. application Ser. No. 07/514,468, filed Apr. 25, 1990, now abandoned, all of which are hereby incorporated by reference.

The use of metal chelates as contrast agents for magnetic resonance, x-ray, ultrasound, and radiodiagnostic imaging is well known. Metal chelates of the transition metal and lanthanide metal ions are of primary interest due to their strong paramagnetic and x-ray absorbing properties as well as others. Because the free metal ions are in general more toxic, these type of pharmaceuticals are prepared in the form of chelates, i.e. the metal ions are complexed, typically by organic ligands. Examples of these organic ligands are linear and macrocyclic poly-aminopolycarboxylic acids and their derivatives. Unfortunately, in many cases there are also toxicity problems with the free organic ligand. Thus, even the use of metal chelates as contrast agents may cause toxicity problems to the extent that free metal and/or free organic ligand may both be present in the blood following introduction of the chelate.

The European patent 0270483 discloses the use of a formulation excipient of the formula

$M_x[M'(L)]_y$, which is described as the metal (M=e.g. sodium) salt of a less toxic metal (M'=e.g. zinc, copper or calcium) chelate, wherein L may or may not be the organic ligand with which the paramagnetic or heavy metal is complexed. This excipient is disclosed as a scavenger for the free metal ions, but no mention is made of scavenging free organic ligand. Indeed, this European patent suggests and claims the addition of free ligand to enhance safety.

In WO 89/00052 entitled "Metal-Ligand Chelates Safety Enhancement—Used in Magnetic Resonance Imaging or X-ray Contrast Agents, by Addition of Calcium Ions", it is claimed that the use of effective amounts of calcium in the form of, calcium chloride, calcium gluconate, or balanced salt solutions substantially reduces the toxicity without the need to add additional ligand. The potential toxicity from free metal ion and/or organic ligand was not discussed.

In accordance with the present invention novel excipients for metal chelate contrast agents, M(L), wherein M is a contrast metal and L is a chelating ligand, for magnetic resonance, x-ray, ultrasound and radiodiagnostic imaging, and compositions and methods utilizing such excipients, are disclosed. These novel excipients have the formula

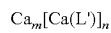
$X_m[X'(L')]_n$,   I wherein X and X' are each independently calcium or zinc; L' is an organic ligand which may be the organic ligand, L, employed in the metal chelate contrast agent or another organic ligand which has a greater affinity for the metal, M, than for calcium or zinc; and wherein m and n are independently selected from 1, 2 or 3. This salt of the complex of the organic ligand is a highly useful excipient for metal chelate contrast agents in that this single excipient has been found to scavenge free metal ions and free organic ligand, thereby enhancing the safety of such contrast agents and methods employing same.

The present invention pertains to novel excipients for metal chelate contrast agents, compositions of contrast agents complexed with such excipients and methods of imaging employing same. Unexpectedly, the novel excipient of the present invention, comprising the salt of the complex of an organic ligand, has been found to scavenge free metal and free organic ligand. Preferably, the excipient comprises the calcium salt of the calcium complex of the ligand shown as

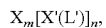
$Ca_m[Ca(L')]_n$ wherein m, n and L' are as defined above. Since the excipients of the present invention are dual-functioning scavengers and are much safer than the free metal ions and free ligands they scavenge, significantly less toxic contrast agents and methods of imaging are provided.

This dual-functioning phenomenon is additionally advantageous in that the possible toxicity resulting from any dissociation of a metal chelate contrast agent, M(L), which may occur while in storage prior to use is also alleviated. Thus, products with enhanced safety and shelf-life are provided by use of the present excipients.

In viewing the dual scavenging activity of the present excipient

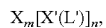
$X_m[X'(L')]_n$, it is believed that the calcium or zinc complex, X' (L'), reacts with the toxic metal ion of the contrast agent by a metal ion exchange process. The free calcium or zinc ion of the excipient forms a complex with free organic ligand that may be present. No other new species are expected to form in situ utilizing this excipient. The calcium or zinc complex salts of formula I are readily prepared by reacting the desired organic ligand in solution with an excess of a calcium salt, e.g., calcium carbonate, calcium chloride, calcium acetate, zinc chloride, zinc acetate and the like.

Thereafter, the present excipients can be employed in compositions with any metal chelate contrast agent comprising a metal ion and an organic ligand. This can be accomplished, using known techniques, by adding the calcium or zinc complex salt of formula I to a solution of the metal chelate contrast agent, as more clearly illustrated in the Examples.

As would be understood by those working in this art, the organic ligand, L', should be selected so that the complexes it forms, i.e., Ca(L'), Zn(L') and/or M(L') are well tolerated. Suitable organic ligands include but are not limited to linear or macrocyclic polyaminopoly-carboxylic acids and derivatives thereof. One preferred group metal chelate contrast agents and imaging methods of the present invention employ organic ligands which are 1-substituted-1,4,7-triscarboxymethyl-1,4,7,10-tetraazacyclododecane and derivatives thereof, as disclosed in U.S. Pat. No. 4,885,363 and pending applications U.S. Ser. No. 454,883, filed Dec. 22, 1989 entitled "10-(2'-Hydroxy-3'-Alkoxy-1,4,7-Triscarboxy-methyl-1,4,7,10-Tetraazacyclododecanes" and U.S. Ser. No. 454,890, filed Dec. 22, 1989 entitled 10-(2'-Hydroxy-3'-Polyoxaalkyl)-1,4,7-Triscarboxy-methyl-1,4,7,10-Tetraaza cyclododecane", incorporated herein by reference, which have the general formula

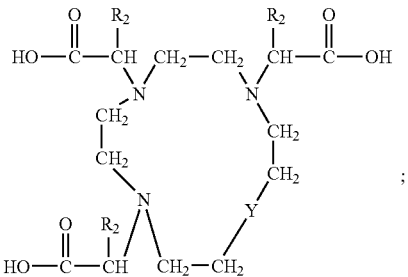

where Y is oxygen or

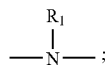

$R_1$ and $R_2$ are each independently hydrogen, alkyl, arylalkyl, aryl, alkoxy, hydroxyalkyl, hydroxyalkoxy

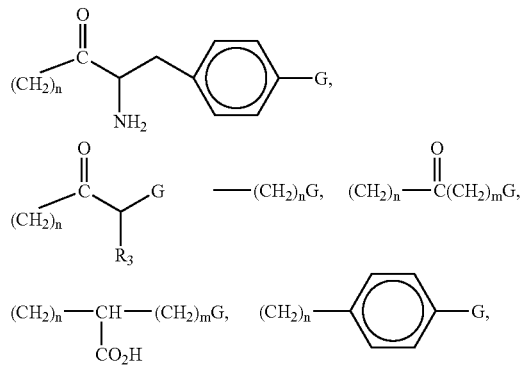

wherein G is $NH_2$, NCS,

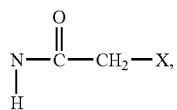

$CO_2H$, $NHR_4$, $N(R_4)_2$, CN, wherein $R_4$ is alkyl or hydroxyalkyl, hydroxyalkoxy,

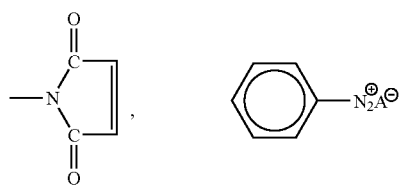

(where A is an anion),

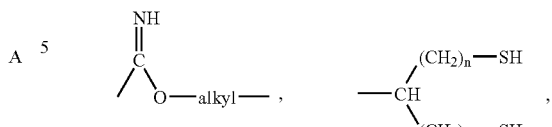

wherein n and m are zero or an integer from one to five, $R_3$ is hydrogen, hydroxyalkyl, alkoxy, alkyl, aryl, arylalkyl or hydroxyalkoxy and X is chloro, bromo or iodo.

$R_1$ and $R_2$ are hydrogen in a preferred embodiment for forming a Gd(III) chelate useful in general purpose magnetic resonance imaging. The most preferred emobodiment for forming a Gd(III) chelate is when $R_1$ is hydroxyalkyl or when $R_1$ is

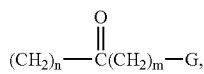

wherein n is 1, m is 0, G is $NHR_4$ wherein $R_4$ is alkyl. Thus, preferred ligands from this group are 1,4,7,10-tetraazacyclododecane-1,4,7-triacetic acid, i.e., DO3A, 1,4,7-tris-(carboxymethyl)-10-(2'-hydroxypropyl)-1,4,7,10-tetraazacyclododecane, i.e., HP-DO3A, and 1,4,7-tris(carboxymethyl)-1,4,7,10-tetraazacyclododecane.

Another group of suitable ligands are disclosed in U.S. Pat. No. 4,647,447 which describes the complex salts

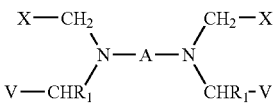

or $N(CH_2X)_3$ wherein
X is —COOY, $PO_3HY$ or —CONHOY;
Y is a hydrogen atom, a metal ion equivalent and/or a physiologically biocompatible cation of an inorganic or organic base or amino acid;
A is —$CHR_2$—$CHR_3$—, —$CH_2CH_2(ZCH_2$—$CH_2)_m$—,

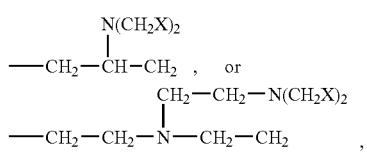

wherein X is as defined above;
each $R_1$ is hydrogen or methyl;
$R_2$ and $R_3$ together represent a trimethylene group or a tetramethylene group or individually are hydrogen atoms, lower alkyl groups (e.g., 1-8 carbons), phenyl groups, benzyl groups or $R_2$ is a hydrogen atom and $R_3$ is —$(CH_2)_p$—

$C_6H_4$—W-protein where p is 0 or 1, W is —NH—, —NH-COCH$_2$— or —NHCS—, protein represents a protein residue;

m is 1, 2 or 3;

Z is an oxygen atom or a sulfur atom or the group NCH$_2$X or NCH$_2$CH$_2$OR$_4$ wherein X is as defined above and R$_4$ is C$_{1-8}$ alkyl;

V is X or is —CH$_2$OH, —CONH(CH$_2$)$_n$X or —COB, wherein X is as defined above, B is a protein or lipid residue, n is an integer from 1 to 12, or if R$_1$, R$_2$ and R$_3$ are each hydrogen; then both V's together form the group

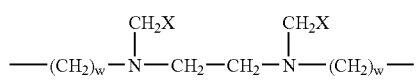

where X is as above, w is 1, 2 or 3, provided that at least two of the substituents Y represent metal ion equivalents of an element with an atomic number of 21 to 29, 42, 44 or 57 to 83. Preferred ligands from U.S. Pat. No. 4,647,447 include 1,4,7,10-tetraazacyclododecane-N,N'N",N"'-tetraacetic acid, i.e., DOTA, and diethylene triamine pentaacetic acid, i.e., DTPA.

Also related to the U.S. Pat. No. 4,647,447 ligands are diethylenetriamine pentaacetic acid-bis methylamide (DTPA-BMA), which can be shown as

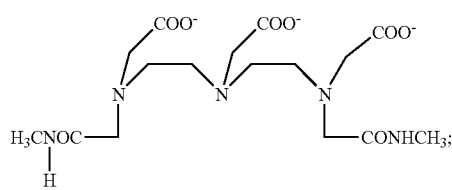

DTPA-bis morpholino amide ((a) below); and DTPA-bis 1,2-dihydroxypropylamide ((b) below)

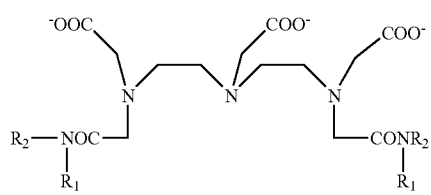

a) R$_1$ and R$_2$ together with nitrogen to which they are attached form morpholino, b) R$_1$ is hydrogen and R$_2$ is

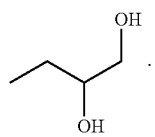

Another group of ligands suitable for use with the present excipients/compositions/methods is disclosed in European Application 0 255 471 A1. That application discloses macrocycles of the formula

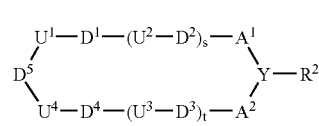

wherein
Y is N or P;
A$^1$ and A$^2$ are each optionally branched C$_{2-6}$ alkylene;
U$^1$, U$^2$, U$^3$ and U$^4$ are each a single bond or optionally branched C$_{1-6}$ alkylene;
D$^1$, D$^2$, D$^3$, D$^4$ are each O, S, C$_{1-6}$ alkylene or NR$_7$;
R$_7$ is hydrogen or C$_{1-4}$ alkylene having a COOR$^1$ terminal group;
R$^1$ is hydrogen or a metal ion equivalent;
D$^5$ is D$^1$ or CHR$^5$, where R$^5$ can be hydrogen or optionally unsaturated C$_{1-20}$ alkylene which may include imino, phenyleneoxy, phenyleneimino, amido, ester, O, S and/or N optionally substituted with OH, SH imino and/or amino and may carry a terminal functional group (optionally bonded to a macromolecule B);
s and t are each 0-5;
R$_2$ is hydrogen, optionally substituted C$_{1-16}$ alkyl, acyl, acylalkyl (optionally substituted by one or more OH or lower alkoxy groups), —CH$_2$—X—V, B or CH$_2$COB where X is CO, optionally branched C$_{1-10}$ alkylene (optionally substituted by 1 or more OH or lower alkoxy groups) or optionally branched C$_{2-23}$ alkylene interrupted by O;
V is NR$^3$R$^4$ or COOR$^6$;
R$^3$ and R$^4$ are each hydrogen, C$_{1-16}$ alkyl (optionally substituted by 1 or more OH or lower alkoxy groups) or together complete a 5-6 membered heterocycle optionally containing another heteroatom;
R$_6$ is hydrogen, C$_{1-16}$ saturated, unsaturated, linear branched or cyclic hydrocarbyl, aryl or aralkyl;
R$_2$ or R$_3$ can be bonded by a C$_{2-20}$ alkylene chain (optionally having a terminal carbonyl group, optionally interrupted by 1 or more O or R$^1$ carboxymethylimino, or substituted by one or more OH, lower alkoxy or carboxy lower alkyl groups) to a second macromolecule of the formula

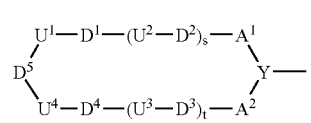

which second macromolecule D' can be the same as or different from the macromolecule of D.

As described above, the excipients of the present invention can be employed with any metal chelate contrast agent. In one embodiment they are used with a contrast agent comprising an organic ligand of formula A complexed with a paramagnetic metal atom and used as relaxation enhancement agents for magnetic resonance imaging. These agents, when administered to a mammalian host (e.g., humans) distribute in various concentrations to different tissues, and catalyze relaxation of protons (in the tissues) that have been excited by the absorption of radiofrequency energy from a magnetic resonance imager. This acceleration of the rate of relaxation of the excited protons provides for an image of different contrast when the host is scanned with a magnetic resonance imager. The magnetic resonance imager is used to record images at various times generally before and after administration of the agents, and the differences in the images created by the agents' presence in tissues are used in diagnosis. In proton magnetic resonance imaging, paramagnetic metal atoms such as gadolinium(III), dysprosium(III), manganese(II), manganese(III) chromium(III), iron(II) and iron(III) (all are paramagnetic metal atoms with a symmetrical electronic configuration) are preferred as metals complexed by the ligands of formula I; gadolinium(III) is most preferred due to the fact that it has the highest paramagnetism, low toxicity, and high lability of coordinated water.

Exemplary contrast agents which will be greatly enhanced when employed in a composition including a pharmaceutically acceptable carrier and an excipient of the present invention include Gadoteridol which is Gd(HP-DO3A), Dotarem which is N-methylglucamine[Gd(DOTA)], Magnevist which is di-N-methylglucamine[Gd(DTPA)] and Gadodiamide which is Gd(DTPA-BMA), Gd(DTPA)-bis morpholino-amide, Gd(DTPA)-bis 1,2-dihydroxypropylamide.

Additionally, the excipients of formula I are conveniently employed with ligands of formula A which are complexed with a lanthanide (atomic number 58 to 71) and used as chemical shift agents in magnetic resonance imaging or in magnetic resonance in vivo spectroscopy.

Excipients of formula I are also conveniently employed with contrast elements including yttrium and the transition series (atomic number 21-29).

While the above-described uses for the excipients of formula I and contrast agents including same are preferred, those working in the medical diagnostic arts will appreciate that the excipients can also be used with contrast agents in x-ray imaging, radionuclide imaging and ultrasound imaging.

As mentioned previously excipients, compositions and methods wherein X=X'=calcium are preferred and these excipients, compositions and methods where L'=L are most preferred.

As described previously, contrast agents which include the excipient of formula I can be easily prepared by adding the calcium or zinc complex salt into the metal chelate contrast agent solution. Preferably the so-formed solution is maintained at about pH neutral. The excipient/contrast agent composition can be prepackaged in combination or the present excipient can be added to the contrast solution directly before use. Typically the mole ratio of the calcium or zinc complex salt to the contrast agent is about 0.05-10 percent.

The following Examples illustrate specific embodiments of the present invention, however, it is understood that the invention should not be limited to the details therein.

EXAMPLE 1

Calcium bis[1,4,7,10-tetraazacyclododecane-1,4,7-triacetatocalcium(II)], Ca[Ca(DO3A)]$_2$*

Twenty millimoles (7.67 g) of DO3A was dissolved in 32 mL of water and 32 mmoles (3.18 g) of calcium carbonate was added slowly. The solution was heated under reflux at 80° C. for 2 hours and it was cooled to room temperature and filtered to remove excess solid calcium carbonate. The solution was then rotary evaporated to dryness and placed in a 75° C. vacuum oven (5 mm Hg) for 24 hours. A glass-like solid was obtained in 94 percent yield.

Analysis calc'd Ca$_3$C$_{28}$H$_{46}$N$_8$O$_{12}$ (8% H$_2$O): C, 38.58; H, 6.15; N, 12.85.

Found: C, 38.17; H, 5.99; N, 12.83.

*DO3A=1,4,7,10-tetraazacyclododecane-1,4,7-triacetate

EXAMPLE 2

Calcium bis[1,4,7-tris(carboxymethyl)-10-(2'-hydroxy)propyl-1,4,7,10-tetraazacyclododecanato-calcium(II)], Ca[Ca(HP-DO3A)]$_2$**

The ligand HP-DO3A, containing 3.5 percent water by elemental analysis data, (0.518 g, 1.24 mmol) was dissolved in 10 mL water at room temperature and solid calcium carbonate (0.204 g, 2.03 mmol) was added to it slowly with stirring. The cloudy solution was heated at 90° C. for 2.5 hours, cooled, centrifuged, and filtered. The filtrate was evaporated under vacuum to dryness to give 0.56 g of white solid. The solid was recrystallized in water:acetone (1:3 v/v) mixture and dried in vacuo at room temperature.

Analysis calc'd Ca$_3$C$_{34}$H$_{58}$N$_8$O$_{14}$ (12% H$_2$O): C, 39.50; H, 6.85; N, 10.84.

Found: C, 39.66; H, 6.83; N, 10.76.

**HP-DO3A=1,4,7-tris(carboxymethyl)-10-(2'-hydroxy)propyl-1,4,7,10-tetraazacyclo-dodecanoate.

EXAMPLE 3

Calcium[1,4,7,10-tetraazacyclododecane-1,4,7-10-tetraacetatocalcium(II)], Ca[Ca(DOTA]*

Twenty millimoles of DOTA is dissolved in 40 mL of water and 44 mmoles of CaCO$_3$ is added slowly. The solution is heated under reflux at 80° C. for 2 hours and it is cooled to room temperature and filtered to remove excess solid CaCO$_3$. The solution is then rotary evaporated to dryness and placed in a 75° C. vacuum oven (5 mm Hg) for 24 hours. A white solid is obtained.

*DOTA=1,4,7,10-tetraazacyclododecane-N,N',N'',N'''-tetraacetate

EXAMPLE 4

Triscalcium bis[N,N'-bis[2-[bis(carboxymethyl)-amino]ethylglycinatecalcium(II)], Ca$_3$[Ca(DTPA)]$_2$**

Twenty millimoles of DTPA is dissolved in 40 mL of water and 55 mmoles of CaCO$_3$ is added slowly. The solution is heated under reflux at 80° C. for 2 hours and it is cooled to room temperature and filtered to remove excess solid CaCO$_3$. The solution is then rotary evaporated to dryness and placed in a 75° C. vacuum oven (5 mm Hg) for 24 hours. A white solid is obtained.

**DTPA =N,N-bis[2-[bis(carboxymethyl)-amino]ethyl-glycinate

EXAMPLE 5

The relative toxicities of free metal, free ligand, metal chelate contrast agent and excipient of the present invention were determined by injecting samples of each into the tail vein of Charles River CD-1 mice (18-23 g, 25-35 days) at 0.02 mL/g. The observation period was 14 days.

The results are summarized in Table 1.

TABLE 1

Intravenous Acute Tolerance in Mice ($LD_{50}$ Values) for $Gd(OH)_3$, DO3A, DOTA, Gd(DO3A), Gd(DO3A) formulated, Gd(HP-DO3A), Gd(HP-DO3A) formulated, Ca[Ca(DO3A)]$_2$, Ca[Ca(HP-DO3A)]$_2$, and $CaCl_2$ at the Physiologic pH.

| Compound | $LD_{50}$ (mMol/kg) |
|---|---|
| $Gd(OH)_3$ | 0.1 |
| DO3A | 0.12 |
| HP-DO3A | 0.11 |
| DOTA | 0.18 |
| Gd(DO3A) | 5.7 |
| Gd(DO3A), formulated[a] | 7.4 (male) |
| | 8.5 (female) |
| Gd(HP-DO3A) | 10 |
| Gd(HP-DO3A), formulated[b] | 10.7 (male) |
| | 13.6 (female) |
| Ca[Ca(DO3A)]$_2$ | 1.6 |
| Ca[Ca(HP-DO3A)]$_2$ | 1.3 |
| $CaCl_2$ | 1.5 |

[a]The formulation consists of Gd(DO3A), 0.5 M; Ca[Ca(DO3A)]$_2$, 0.25 mM; Tris Buffer, 10 mM (pH 7.4).
[b]The formulation consists of Gd(HP-DO3A), 0.5 M; Ca[Ca(HP-DO3A)]$_2$, 0.25 mM; Tris Buffer, 10 mM (pH 7.4).

The data illustrate that the complexed Gd(DO3A) (i.e., metal chelate contrast agent) and calcium complex salt (i.e., excipient) were highly tolerated. Therefore, when using the calcium complex salt of the present invention as the excipient, the amounts of free metal and free ligand are greatly reduced and any excesses of chelated contrast agent or excipient are well tolerated providing contrast methodology with enhanced safety.

EXAMPLE 6

The following novel diagnostic formulation was prepared by combining the known diagnostic agent, Gadoteridol, with the excipient of Example 2 using the procedure which follows:

| Ingredient | Amount (per ml) |
|---|---|
| Gadoteridol[1] (diagnostic agent) | 558.6 mg |
| Calteridol Calcium[2] (novel excipient) | 0.46 mg |
| Tromethamine (buffer) | 1.21 mg |
| 1N NaOH solution | as needed for pH adjustment |
| 1N HCl solution | as needed for pH adjustment |
| Water for Injection USP q.s. | 1.0 ml |

[1]Gadolinium(III) 1,4,7-tris(carboxymethyl)-10-(2'-hydroxypropyl)-1,4,7,10-tetraazacyclododecane
[2]Ca[Ca(HP-DO3A)]$_2$ excipient of Example 2 above.

Procedure: About 60% of the necessary water was heated to between 48 and 52° C. and vigorously agitated while adding the buffer (tromethamine) and excipient (calteridol calcium). Thereafter, the diagnostic agent (gadoteridol) was added slowly and the agitation was continued for about 1 hour while maintaining the temperature at 48-52° C. The so-prepared solution was cooled to 20-25° C. and the pH was adjusted to between 7.3 and 7.5 (7.4 optimum) using HCl solution and/or NaOH solution as necessary. The balance of the water was added and the pH rechecked/readjusted. The solution was filtered through a sterile 0.2 micrometer membrane and thereafter sterilized and stored at controlled room temperature (15-30° C.).

EXAMPLE 7

A novel diagnostic composition for Dotarem, i.e., N-methylglucamine [Gd(DOTA)], was prepared using the procedure above in Example 6 but substituting Dotarem for Gadoteridol and substituting the excipient of Example 3, Ca[Ca(DOTA)], for the calteridol calcium.

EXAMPLE 8

A novel diagnostic composition for Magnevist, i.e., (N-methylglucamine)$_2$ [Gd(DTPA)], was prepared using the procedure of Example 6 but substituting Magnevist for Gadoteridol and substituting the excipient of Example 4, Ca$_3$[Ca(DTPA)]$_2$, for the calteridol calcium.

EXAMPLE 9

A novel diagnostic composition for Gadodiamide, i.e., Gd(DTPA-bis methylamide), was prepared using the procedure of Example 6 but substituting Gadodiamide for Gadoteridol and substituting an excipient Ca[Ca(DTPA-bis methylamide)]$_2$, prepared using the methodology of Example 2.

EXAMPLE 10

A novel diagnostic composition was prepared for the contrast agent gadolinium DTPA bis morpholinoamide using the procedure of Example 6 substituting this agent for Gadoteridol and substituting an excipient, Ca[Ca(DTPA bis morpholinoamide)]$_2$ prepared using the methodology of Example 2.

EXAMPLE 11

A novel diagnostic composition was prepared for the contrast agent gadolinium (DTPA 1,2-di-hydroxypropylamide) using the procedure of Example 6 substituting this agent for Gadoteridol and substituting an excipient, Ca[Ca(DTPA 1,2-di-hydroxypropylamide)]$_2$, prepared using the methodology of Example 2.

What is claimed:

1. A composition for use in magnetic resonance, x-ray, ultrasound and radio-diagnostic imaging comprising:
a contrast agent of the formula

M(L)

where M is a metal ion and L is an organic ligand of the formula

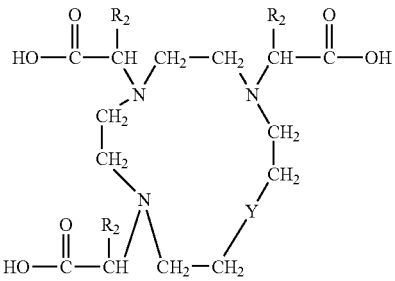

wherein
Y is

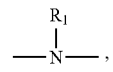

$R_1$ is hydroxypropyl and $R_2$ is H; and
a complex salt excipient of the formula $X_m[X'(L')]_n$ wherein X and X' are calcium; L' is

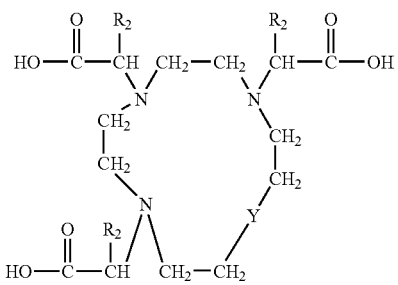

wherein
Y is

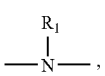

$R_1$ is hydroxypropyl and $R_2$ is H;
m is 1 and n is 2.

2. The composition of claim 1 wherein L and L' are each 1,4,7-tris(carboxymethyl)-10-(2'-hydroxypropyl)-1,4,7,10-tetraazacyclododecane.

3. The composition of claim 1 wherein the mole ratio of said complex salt excipient to said contrast agent is between about 0.05 and 10 percent.

4. The composition of claim 1 wherein said metal ion is selected from paramagnetic metal atoms, lanthanide series elements, yttrium, and the transition series elements.

5. The composition of claim 4 wherein said paramagnetic metals are selected from gadolinium(III), dysprosium(III), manganese(II), manganese(III), chromium(III), iron(II) and iron(III).

6. The composition of claim 1 wherein said metal ion M complexed with an organic ligand is gadolinium(III) 1,4,7-tris(carboxymethyl)-10-(2'-hydroxypropyl)-1,4,7,10-tetraazacyclododecane and said excipient is calcium bis[1,4,7-tris(carboxy-methyl)-10-(2'-hydroxypropyl)-1,4,7,10-tetraazacyclododecanatocalcium(II)].

* * * * *